US00PP35937P2

(12) United States Plant Patent
Uebelhart

(10) Patent No.: US PP35,937 P2
(45) Date of Patent: Jul. 2, 2024

(54) ***VERBENA* PLANT NAMED 'JELVERWHIT'**

(50) Latin Name: *Glandularia canadensis*
Varietal Denomination: Jelverwhit

(71) Applicant: JELITTO STAUDENSAMEN GmbH, Schwarmstedt (DE)

(72) Inventor: Georg Uebelhart, Salzhausen (CH)

(73) Assignee: JELITTO STAUDENSAMEN GmbH, Schwarstedt (DE)

( * ) Notice: Subject to any disclaimer, the term of this patent is extended or adjusted under 35 U.S.C. 154(b) by 0 days.

(21) Appl. No.: 18/383,313

(22) Filed: Oct. 24, 2023

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
See application file for complete search history.

*Primary Examiner* — Susan McCormick Ewoldt
(74) *Attorney, Agent, or Firm* — C. Anne Whealy

(57) ABSTRACT

A new and distinct cultivar of *Verbena* plant named 'Jelverwhit', characterized by its relatively compact, upright to broadly outwardly spreading plant habit; vigorous growth habit and rapid growth rate; freely branching habit; early and freely flowering habit; bright white-colored flowers that are highly fragrant; and good garden performance and winter-hardiness.

2 Drawing Sheets

Figure 1:
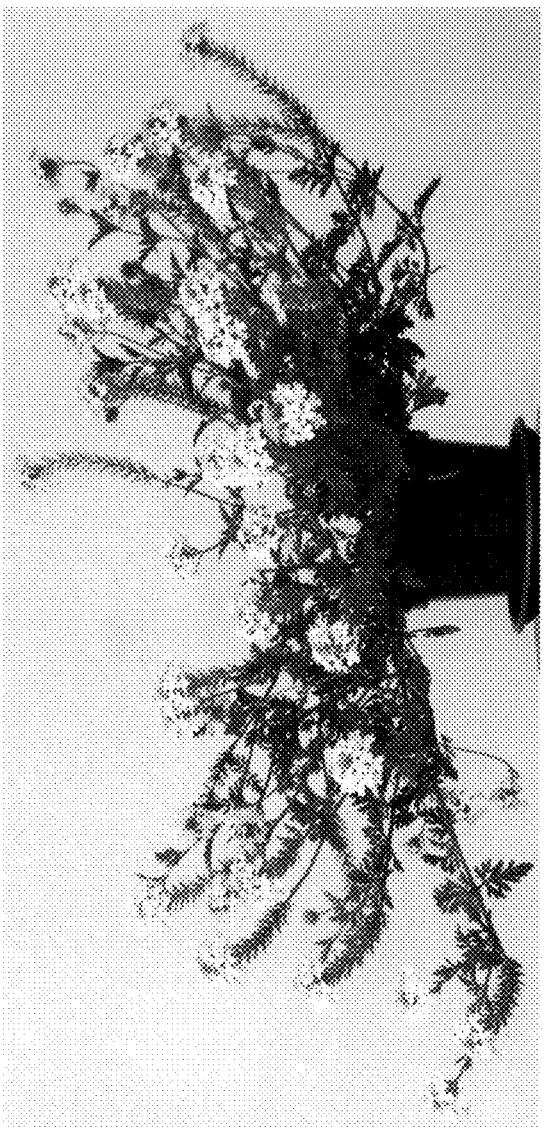

Botanical designation: *Glandularia canadensis.*
Cultivar denomination: 'JELVERWHIT'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Jelitto Staudensamen GmbH of Schwarmstedt, Germany on Mar. 6, 2023, application number 2023/0576. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Verbena* plant, botanically known as *Glandularia canadensis* (syn. *Verbena canadensis*) and hereinafter referred to by the name 'Jelverwhit'.

The new *Verbena* plant is a product of a planned breeding program conducted by the Inventor in Schwarmstedt, Germany. The objective of the breeding program is to create new freely branching and early flowering *Verbena* plants with numerous large and attractive flowers and winter hardiness.

The new *Verbena* plant originated from an open-pollination during the summer of 2016 in Schwarmstedt, Germany of a proprietary selection of *Glandularia canadensis* identified as code number V16002, not patented, as the female, or seed, parent with an unknown proprietary selection of *Glandularia canadensis*, as the male, or pollen, parent. The new *Verbena* plant was discovered and selected by the Inventor as a single flowering plant within the progeny of the stated open-pollination in a controlled greenhouse environment in Schwarmstedt, Germany during the summer of 2018.

Asexual reproduction of the new *Verbena* plant by terminal vegetative cuttings in a controlled greenhouse environment in Hendrik-Ido-Ambacht, The Netherlands since 2020 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Jelverwhit'. These characteristics in combination distinguish 'Jelverwhit' as a new and distinct *Verbena* plant:

1. Relatively compact, upright to broadly outwardly spreading plant habit.
2. Vigorous growth habit and rapid growth rate.
3. Freely branching habit.
4. Early and freely flowering habit.
5. Bright white-colored flowers that are highly fragrant.
6. Good garden performance and winter-hardiness.

Plants of the new *Verbena* differ primarily from plants of the female parent selection in the following characteristics:

1. Plants of the new *Verbena* are more uniform than plants of the female parent selection.

2. Flower color of plants of the new *Verbena* is more stable than flower color of plants of the female parent selection.
3. Flowers of plants of the new *Verbena* are more fragrant than flowers of plants of the female parent selection.
4. Plants of the new *Verbena* are more winter-hardy than plants of the female parent selection.

Plants of the new *Verbena* can be compared to plants of the *Verbena* X *hybrida* 'Balendwite', disclosed in U.S. Plant Pat. No. 30,641. In side-by-side comparisons, plants of the new *Verbena* differ primarily from plants of 'Balendwite' in the following characteristics:

1. Plants of the new *Verbena* are more outwardly spreading than plants of 'Balendwite'.
2. Plants of the new *Verbena* have larger flowers than plants of 'Balendwite'.
3. Plants of the new *Verbena* are more winter-hardy than plants of 'Balendwite'.

Plants of the new *Verbena* can also be compared to plants of the *Glandularia canadensis* 'Snow Flurry', not patented. In side-by-side comparisons, plants of the new *Verbena* differ primarily from plants of 'Snow Flurry' in the following characteristics:

1. Plants of the new *Verbena* have larger flowers than plants of 'Snow Flurry'.
2. Flowers of plants of the new *Verbena* are fragrant whereas flowers of plants of 'Snow Flurry' are not fragrant.
3. Plants of the new *Verbena* are more winter-hardy than plants of 'Snow Flurry'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph on the first sheet (FIG. 1) is a side perspective view of a typical flowering plant of 'Jelverwhit' grown in a container.

Figure 2:
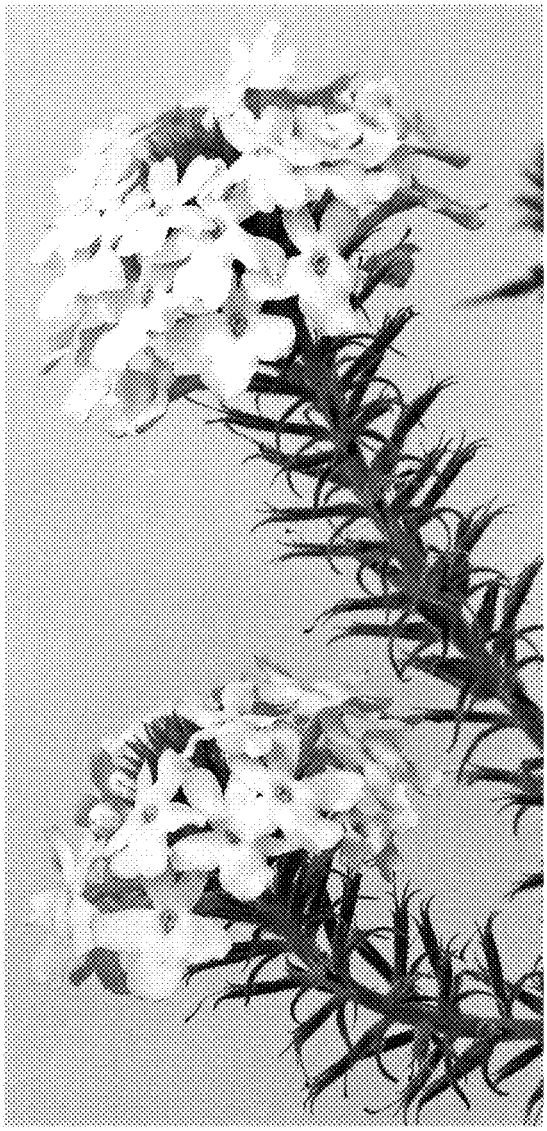

The photograph on the second sheet (FIG. 2) is a close-up view of typical inflorescences of 'Jelverwhit'.

DETAILED BOTANICAL DESCRIPTION

The aforementioned photographs and following observations, measurements and values describe plants grown in 15-cm containers during the summer in an outdoor nursery in Hendrik-Ido-Ambacht, The Netherlands and under cultural practices typical of commercial *Verbena* production. During the production of the plants, day temperatures ranged from 13 C to 22 C and night temperatures ranged from 3 C to 13 C. Plants were pinched one time before planting and were four months old when the photographs and description were taken. In the description, color references are made to The Royal Horticultural Society Colour Chart, Sixth Edition, except where general terms of ordinary dictionary significance are used.

Botanical classification: *Glandularia canadensis* 'Jelverwhit'.

Parentage:

*Female, or seed, parent*.—Proprietary selection of *Glandularia canadensis* identified as code number V16002, not patented.

*Male, or pollen, parent*.—Unknown proprietary selection of *Glandularia canadensis*, not patented.

Propagation:

*Type*.—Terminal vegetative cuttings.

*Time to initiate roots, summer and winter*.—About two weeks at temperatures about 20 C.

*Time to produce a rooted young plant, summer*.—About four weeks at temperatures about 20 C.

*Time to produce a rooted young plant, winter*.—About five weeks at temperatures about 20 C.

*Root description*.—Medium in thickness, fibrous; typically white in color, actual color of the roots is dependent on substrate composition, water quality, fertilizers, substrate temperature and age of roots.

*Rooting habit*.—Freely branching; medium density.

Plant description:

*Plant habit*.—Relatively compact, upright to broadly outwardly spreading plant habit; freely branching habit with about eleven primary lateral branches each with about four secondary lateral branches; dense and bushy plant habit; vigorous growth habit and rapid growth rate.

*Plant height, soil level to top of foliar plane*.—About 30.8 cm.

*Plant height, soil level to top of floral plane*.—About 36.4 cm.

*Plant diameter*.—About 84.6 cm.

Lateral branch description:

*Length* (*excluding inflorescences*).—About 15.4 cm.

*Diameter*.—About 3 mm.

*Internode length*.—About 4.9 cm.

*Strength*.—Strong.

*Aspect, primary lateral branches*.—Erect to horizontal.

*Aspect, secondary lateral branches*.—About 25 to 35 degrees from primary lateral branch axis.

*Texture and luster*.—Densely pubescent; moderately glossy.

*Color, developing, upper and lower surfaces*.—Close to 144B.

*Color, developed, upper and lower surfaces*.—Close to 144A.

Leaf description:

*Arrangement*.—Opposite, simple.

*Length*.—About 4.2 cm.

*Width*.—About 3.6 cm.

*Shape*.—Broadly ovate, in overall outline.

*Apex*.—Acute.

*Base*.—Attenuate.

*Margin*.—Deeply dissected; sinuses deep in depth and divergent.

*Texture and luster, upper surface*.—Sparsely pubescent; slightly glossy.

*Texture and luster, lower surface*.—Sparsely pubescent; matte.

*Venation pattern*.—Pinnate.

*Color*.—Developing leaves, upper surface: Close to 144A. Developing leaves, lower surface: Close to 144B. Fully expanded leaves, upper surface: Close to NN137C; venation, close to 146C. Fully expanded leaves, lower surface: Close to 138B; venation, close to 146D.

*Petioles*.—Length: About 1.2 cm. Diameter: About 2 mm. Strength: Strong. Texture and luster, upper surface: Sparsely to moderately pubescent; slightly glossy. Texture and luster, lower surface: Sparsely to moderately pubescent; matte. Color, upper surface: Close to N144D; margins, close to 137A to 137B. Color, lower surface: Close to 144B.

Flower description:

*Flower arrangement and habit*.—Salverform flowers arranged in hemispherical terminal inflorescences; inflorescences dense and mounding; numerous inflorescences per plant; flowers face upward or slightly outwardly depending on position in the inflorescence; freely flowering habit with about 100 flowers developing per inflorescence and about 6,500 flowers and flower buds developing per plant during the flowering season; flowers sessile.

*Fragrance*.—Fragrant; sweet and pleasant.

*Natural flowering season*.—Plants flower continuously from the spring through the fall in Germany.

*Flower longevity*.—Individual flowers last about two weeks on the plant; flowers persistent.

*Inflorescence height*.—About 18 cm.

*Inflorescence diameter*.—About 5.4 cm.

*Flower buds*.—Length: About 1.3 cm. Diameter: About 2 mm. Shape: Narrowly oblanceolate. Texture and luster: Moderately to densely pubescent; matte. Color: Immature calyx, close to 145B; immature petals, close to NN155D.

*Flowers*.—Appearance: Salverform, five-parted fused corolla. Diameter: About 1.8 cm by 1.9 cm. Depth: About 2 cm. Throat diameter: About 2 mm. Tube length: About 2 cm. Tube diameter: About 2 mm.

*Corolla*.—Arrangement: Single whorl of five petals, two upper petals and three lower petals; lower 69% of the petals is fused. Petal lobe length, upper petals: About 7 mm. Petal lobe length, lower petals: About 9 mm. Petal lobe width, upper petals: About 4 mm. Petal lobe width, lower petals: About 5 mm; center petal, slightly longer, about 6 mm. Petal lobe shape, all petals: Long and narrowly oblanceolate. Petal lobe apex, all petals: Emarginate. Petal margin, all petals: Entire; not undulate. Petal texture and luster, all petals, upper surface: Smooth, glabrous; slightly velvety; matte. Petal texture and luster, all petals, lower surface: Smooth, glabrous; matte. Throat texture and luster: Moderately pubescent; matte. Tube texture and luster: Sparsely to moderately pubescent; matte. Color, all petals: Petal lobe, when opening, upper and lower surfaces: Close to NN155D. Petal lobe, fully opened, upper and lower surfaces: Close to NN155D; venation, close to NN155D; color does not change with subsequent development. Throat: Close to 145B; venation, close to 145B. Tube: Close to 145C; proximally, close to 157A; venation, close to 145C and 157A.

*Calyx*.—Arrangement: Star-shaped calyx with five fused sepals. Length: About 1.3 cm. Diameter: About 3 mm. Sepal length: About 1.1 cm to 1.3 cm. Sepal width: About 4 mm. Sepal shape: Lanceolate. Sepal apex: Narrowly acute. Sepal margin: Entire. Sepal texture and luster, upper surface: Smooth, glabrous; slightly glossy. Sepal texture and luster, lower surface: Moderately to densely pubescent; matte. Sepal color, when developing, upper and lower surfaces: Close to 157A; venation, close to 144B. Sepal color, fully developed, upper and lower surfaces: Close to 157A; venation, close to 144B.

*Peduncles*.—Length: About 15.7 cm. Diameter: About 2.5 mm. Strength: Strong. Aspect: Mostly upright. Texture and luster: Densely pubescent; moderately glossy. Color: Close to 144A; distally, close to 144C.

*Reproductive organs*.—Stamens: Quantity and arrangement: About four per flower, adnate to corolla tube. Filament length: About 1.5 mm. Filament color: Close to 145D. Anther size: About 0.5 mm by 0.75 mm. Anther shape: Oblong. Anther color: Close to 144C. Pollen amount: Scarce. Pollen color: Close to 150B. Pistils: Quantity: One per flower. Pistil length: About 1.5 cm. Style length: About 1.4 cm. Style color: Close to 150B. Stigma diameter: About 1 mm. Stigma shape: Cleft. Stigma color: Close to 143B. Ovary color: Close to 144D. Seed/fruits: To date, seed and fruit development has not been observed on plants of the new *Verbena*.

Garden performance: Plants of the new *Verbena* have been observed to have good garden performance, to tolerate temperatures ranging from −23 C to 35 C and to be suitable for USDA Hardiness Zones 5 to 10.

Pathogen & pest resistance: To date, plants of the new *Verbena* have not been observed to be resistant to pathogens and pests common to *Verbena* plants.

It is claimed:

1. A new and distinct *Verbena* plant named 'Jelverwhit' as illustrated and described.

* * * * *